United States Patent [19]

Stanko

[11] 4,351,835

[45] Sep. 28, 1982

[54] METHOD FOR PREVENTING BODY FAT DEPOSITION IN MAMMALS

[75] Inventor: Ronald T. Stanko, Pittsburgh, Pa.

[73] Assignee: Montefiore Hospital, Pittsburgh, Pa.

[21] Appl. No.: 249,812

[22] Filed: Apr. 1, 1981

[51] Int. Cl.³ .................... A61K 31/12; A61K 31/19; A61K 31/525

[52] U.S. Cl. ................................. 424/252; 424/317; 424/331

[58] Field of Search ...................... 424/252, 317, 331

[56] References Cited

U.S. PATENT DOCUMENTS 4,158,057 6/1979 Stanko ................................. 424/252

OTHER PUBLICATIONS

Stanko et al., Journal of Laboratory & Clinical Medicine, vol. 91, No. 2, pp. 228-235, Feb., 1978.

Stanko et al., American Gastroenterological Association, vol. 76, No. 1, Jan. 1979, pp. 132-138.

Jamdar et al.–Biochem. J. (Great Britain) 158, pp. 327-334, 1978.

Jamdar et al.–Journal Of Lipid Research, vol. 14, 1973, pp. 509-516.

Schiff, "Diseases Of The Liver", 4th ed., 1975, pp. 824-829.

*Primary Examiner*—Leonard Schenkman
*Attorney, Agent, or Firm*—Thomas H. Murray; Clifford A. Poff

[57] ABSTRACT

A method for reducing the rate of liver triglyceride synthesis and body fat deposition in mammals by orally administering over a prolonged period a therapeutic mixture of effective amounts of pyruvate and dihydroxyacetone to which may be added riboflavin. The method also has the effect of increasing the glycogen-storing capabilities of the liver.

9 Claims, 4 Drawing Figures

METHOD FOR PREVENTING BODY FAT DEPOSITION IN MAMMALS

BACKGROUND OF THE INVENTION

In U.S. Pat. No. 4,158,057, issued June 12, 1979, a method is described for preventing the accumulation of excessive fatty deposits in the livers of mammals. It has long been known that ingestion of ethyl alcohol in mammals, including man, frequently results in the accumulation of excessive fatty deposits in the liver. In many cases, this accumulation tends to become irreversible and may lead to serious consequences, particularly alcohol-induced hepatitis and, ultimately, cirrhosis.

The invention described in the aforesaid U.S. Pat. No. 4,158,057 resides in the discovery that excessive fatty deposits in the liver can be reduced or prevented from occurring by administering a therapeutic composition consisting of a mixture of pyruvate and dihydroxyacetone to which may be added riboflavin. These substances are natural metabolites which occur in the body as a result of normal digestive processes. Heretofore, however, there has been no appreciation of any correlation between the accumulation of fatty deposits in the liver, usually due to the ingestion of alcohol, and the accumulation of fat in other parts of the body.

SUMMARY OF THE INVENTION

In accordance with the present invention, it has now been found, quite surprisingly, that the mixture disclosed in U.S. Pat. No. 4,158,057, when administered for a relatively long period of time, at least 15 days or more, results in a reduction of the rate of hepatic triglyceride generation and body fat deposition for a given diet. The invention is thus useful for impeding overweight conditions in mammals, with or without ingestion of ethanol.

Additionally, it has been found that prolonged ingestion of a mixture of pyruvate and dihydroxyacetone, with or without riboflavin, increases the glycogen-storage capabilities of the liver. Stored glycogen is thus increased for subsequent release into the bloodstream. Stored glycogen has been reported to increase the performance and endurance of athletes.

The above and other objects and features of the invention will become apparent from the following detailed description taken in connection with the accompanying drawings which form a part of this specification, and in which.

Figure 1:
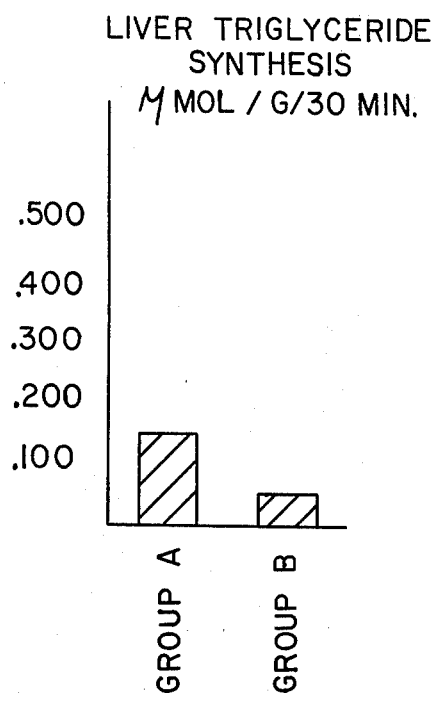
FIG. 1 is a bar graph illustrating the effect of the present invention on liver triglyceride synthesis for the case where no ethanol is ingested.

To demonstrate the efficacy of the invention, a group of rats (Group A) each weighing about 200 grams was fed a standard laboratory diet for a period of 60 days, the diet containing 15% protein, 28% fat and 57% carbohydrate. A second group of rats (Group B) was fed the same diet as Group A except with the addition of a mixture of pyruvate, dihydroxyacetone and riboflavin. The specific mixture comprised 22.5 grams of pyruvate, 22.5 grams of dihydroxyacetone and 2.25 grams of riboflavin per 1000 cubic centimeters of diet. After being on the aforesaid diets for 60 days, each group of rats was injected with radioactive glycerol. About one hour after the injection, the rats were sacrificed, their livers removed, and the radioactive triglyceride generated was determined by chemical analysis. The results are shown in FIG. 1; and it will be noted that the rats in Group B which ingested the mixture of pyruvate, dihydroxyacetone and riboflavin with the same basic diet had a much lower rate of liver triglyceride synthesis. That is, those in Group B had a synthesis rate of about 0.05 millimol per gram per 30 minutes; while those which did not receive the mixture in Group A had a much higher triglyceride synthesis rate of 0.15 millimol per gram per 30 minutes.

Figure 2:
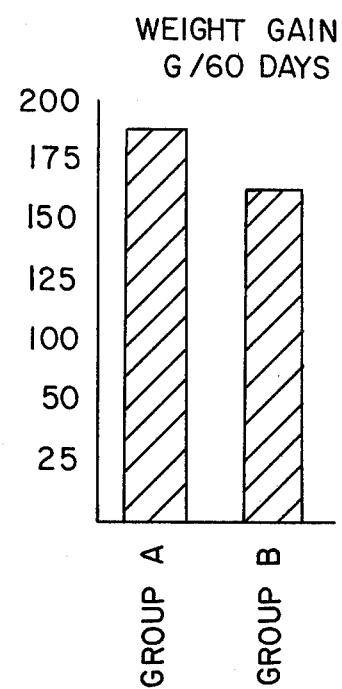
FIG. 2 is a bar graph illustrating the effect of the invention on weight gain for the case where no ethanol is ingested.

More surprising is the effect on weight gain by adding the mixture of pyruvate, dihydroxyacetone and riboflavin to the diet. This is shown in FIG. 2 where, it will be noted, those rats which did not receive the mixture gained almost 190 grams during the 60-day period; whereas those which did receive the agent (Group B) gained only about 160 grams. From this it can be concluded that as the rate of triglyceride synthesis decreases, so also does the total weight gain.

Figure 3:
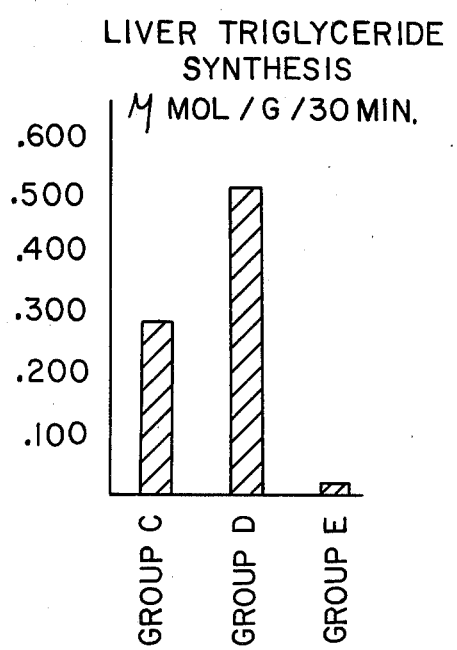
FIG. 3 is a bar graph similar to that of FIG. 2 but illustrating the effect of the invention with the ingestion of ethanol.
Figure 4:
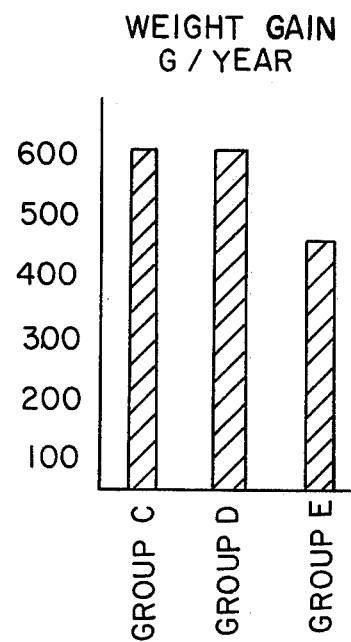
FIG. 4 is a bar graph similar to that of FIG. 2 for the case where ethanol is ingested.

In another group of experiments extending over a period of one year, rats were divided into three groups ranging from 4 to 8 in number. The first group (Group C) was fed a diet comprising 15% protein, 28% fat and 57% carbohydrate, the same as for Groups A and B. The second group (Group D) received the same diet as Group C except that half of the carbohydrate content of the diet was substituted isocalorically with ethanol. The third group (Group E) received the same diet as Group D containing ethanol but with the addition of 22.5 grams of pyruvate, 22.5 grams of dihydroxyacetone and 2.25 grams of riboflavin per 1000 cubic centimeters of diet. The effect of the rate of triglyceride synthesis is shown in FIG. 3. Note that Group D, which ingested ethanol, had a much higher rate of triglyceride synthesis; whereas Group E which ingested ethanol but at the same time ingested the treating agent of the invention had a much, much lower rate of triglyceride synthesis. The synthesis rate was determined with a radioactive precursor in the same manner as described above in connection with Groups A and B. The effect on weight gain is shown in FIG. 4. Note that Groups C and D had the same weight gain over a year's time, which indicates that ingestion of ethanol and the rate of triglyceride synthesis have very little to do with weight gain. In Group E, however, which had the same diet as Group D, weight gain is significantly lower, being on the order of 450 grams per year as contrasted with 600 grams per year for Groups C and D.

While the treating agent in all cases contained riboflavin, it is believed that this latter agent has a minimal effect on weight gain and that substantially the same effect can be obtained with or without the addition of riboflavin. The quantitative effect on weight gain is dependent upon the dosage; however the dosage is not critical per se. In order to obtain any practical effect as regards weight loss, the agent of the invention should be administered, usually for at least 15 days, until a perceptible weight loss is observed for a given diet. An effective treatment for reducing weight gain in mammals is, therefore, provided utilizing natural metabolites readily available at a relatively low cost.

As is known, the liver, in addition to synthesizing triglycerides, also acts as a storage medium for glycogen. Glycogen is known as the emergency fuel since, unlike fat stores, glycogen is readily available and easy to convert back into glucose. That is, glucose brought to the liver from the intestine via the portal vein in converted to glycogen and stored. As the need arises, glucose is re-formed from glycogen and released into the bloodstream. It has been found that by administering the mixture of the invention over a long period of time, the glycogen-storing capability of the liver is increased, accompanied by an increase in the size of the liver. This is shown in the following Table where the glycogen concentration in mg/g of liver tissue and total glycogen are tabulated for the same groups of rats C, D and E described above in connection with FIG. 2, the rats being treated for a period of one year. The livers of four rats in each group were subjected to a standard acid extraction of glycogen after sacrifice.

TABLE

|  | GROUP C | GROUP D | GROUP E |
|---|---|---|---|
| | Glycogen Concentration* | | |
| Rat No. 1 | 13.2 | 16.5 | 37.1 |
| Rat No. 2 | 17.9 | 13.6 | 31.1 |
| Rat No. 3 | 29.9 | 10.4 | 80.8 |
| Rat No. 4 | 25.6 | 30.2 | 40.3 |
| Average value (mg/g) | 21.65 | 17.6 | 47.3 |
| | Total Glycogen** | | |
| Rat No. 1 | 227.7 | 275.3 | 841.4 |
| Rat No. 2 | 225.5 | 199.6 | 602.0 |
| Rat No. 3 | 488.8 | 182.8 | 1624.8 |
| Rat No. 4 | 502.0 | 750.1 | 961.9 |
| Average value (mg) | 361 | 351 | 1007 |

*mg of glycogen per gram of liver tissue
**mg of glycogen

While the effect on individual rats in each group varies substantially, it can be seen from the foregoing Table that all rats in Group E which were treated with the mixture of the invention without ingestion of ethanol had much higher glycogen contents than either those in Group D which ingested ethanol without treatment and those in Group C which neither ingested ethanol nor were treated with the mixture of the invention.

For many years athletes have attempted, by eating large amounts of carbohydrate-laden meals, to increase their glycogen stores prior to an athletic event requiring long endurance or sustained high performance. The use of the mixture of the invention appears to increase greatly the glycogen-storage capability of the liver.

Although the invention has been shown in connection with certain specific embodiments, it will be readily apparent to those skilled in the art that various changes can be made to suit requirements without departing from the spirit and scope of the invention.

I claim as my invention:

1. A method for controlling weight in a mammal, which comprises administering orally to said mammal a therapeutic mixture of pyruvate and dihydroxyacetone in an effective amount to induce a weight loss or to reduce an expected weight gain from a given diet.

2. The method of claim 1 in which said mixture also includes riboflavin.

3. The method of claim 1 wherein said mixture is administered for at least 15 days.

4. The method according to claim 1 wherein said mixture is administered for 60 days.

5. The method according to claim 1 wherein body fat deposition in said mammal is effectively reduced by administering said mixture.

6. The method according to claim 1 wherein glycogen concentration in said mammal is increased above normal by administering said mixture.

7. The method according to claim 1, 4, 5 or 6 wherein the rate of hepatic triglyceride generation in said mammal is effectively reduced by administering said mixture.

8. A method for increasing the glycogen concentration in the liver of a mammal, which comprises administering orally to said mammal effective amounts of a mixture of pyruvate and dihydroxyacetone for a period sufficient to increase glycogen concentration above normal.

9. The method of claim 8 wherein the agent is administered to athletes prior to strenuous athletic events to increase endurance and/or performance.

* * * * *